United States Patent [19]
Asakura et al.

[11] Patent Number: 5,747,069
[45] Date of Patent: May 5, 1998

[54] PERCUTANEOUSLY ABSORBABLE PREPARATION

[75] Inventors: Sotoo Asakura, Kyoto; Sumihisa Kimura, Kawanishi; Kazutake Kado, Toyonaka; Yoshiko Ohishi, Kobe; Takehisa Hata, Nagaokakyo, all of Japan

[73] Assignee: Fujisawa Pharmaceutical Co., Ltd., Osaka, Japan

[21] Appl. No.: 592,307

[22] PCT Filed: Aug. 4, 1994

[86] PCT No.: PCT/JP94/01282

§ 371 Date: Mar. 15, 1996

§ 102(e) Date: Mar. 15, 1996

[87] PCT Pub. No.: WO95/04551

PCT Pub. Date: Feb. 16, 1995

[30] Foreign Application Priority Data

Aug. 10, 1993 [JP] Japan ................... 5-198014
Dec. 16, 1993 [JP] Japan ................... 5-316319

[51] Int. Cl.$^6$ ............................................. A61K 9/06
[52] U.S. Cl. ................ 424/484; 514/183; 514/414; 514/469; 514/944
[58] Field of Search ........................... 424/401, 484; 514/183, 414, 469, 944, 969

[56] References Cited

FOREIGN PATENT DOCUMENTS 0279986  8/1988  European Pat. Off. .

OTHER PUBLICATIONS

JP 63-227520 (1988).

*Primary Examiner*—Jyothsan Venkat
*Attorney, Agent, or Firm*—Oblon, Spivak, McClelland, Maier & Neustadt, P.C.

[57] ABSTRACT

A percutaneously absorbable preparation containing a drug and a percutaneous absorption accelerator comprising a monoglyceride and a fatty acid.

10 Claims, No Drawings

PERCUTANEOUSLY ABSORBABLE PREPARATION

TECHNICAL FIELD

This application is a 371 of PCT/JP94/01282 filed Aug. 4, 1994.

This invention relates to a percutaneously absorbable preparation containing a drug and a percutaneous absorption accelerator comprising a monoglyceride and a fatty acid.

More particularly, this invention relates to a percutaneously absorbable preparation containing a monoglyceride as well as a fatty acid for enhanced cutaneous penetration of an insoluble (insoluble or sparingly soluble in water) drug.

BACKGROUND

For the purpose of improving the percutaneous absorption of an insoluble drug, it is common practice to employ a solubilizer such as Polyethylene Glycol 400 or propylene glycol.

It is also known that monoglycerides of medium-chain fatty acids assist in percutaneous absorption. For example, JP Kokai 63-227520 employs monolaurin, that is 1-monolauroylrac-glycerol, as a percutaneous absorption accelerator.

However, the problem remains that even the use of cutaneous penetration aids such as said solubilizers and monoglycerides of medium-length fatty acids generally does not insure a sufficient percutaneous delivery of drug which are inherently more or less insoluble in water.

There accordingly exists a demand for the development of dosage forms providing for still improved percutaneous absorption.

DISCLOSURE OF INVENTION

After much research for solving the above problem and even to their own surprise, the inventors of this invention discovered that a dramatic enhancement of cutaneous penetration can be achieved by causing a fatty acid to be present in conjunction with a monoglyceride and have perfected this invention.

This invention is now described in further detail.

The percutaneously absorbable preparation of this invention is characterized by containing a drug and a percutaneous absorption accelerator comprising a monoglyceride and a fatty acid.

The preferred monoglyceride for use in this preparation can be selected from among those monoglycerides which are conventionally employed in the pharmaceutical field, thus including glycerides of medium-chain or long-chain fatty acids, whether saturated or unsaturated, typically monocaprin, monolaurin, monomyristin, monopalmitin, monostearin, monoolein, etc., and mixtures thereof. In particular, glycerides of saturated or unsaturated fatty acids containing 10 to 20 carbon atoms are preferred, and monocaprin, monolaurin and monoolein are especially useful.

As preferred examples of the fatty acid for use in this invention, those fatty acids which are conventionally employed in the pharmaceutical field can be mentioned. Typically, medium-chain and long-chain fatty acids, whether saturated or unsaturated, such as capric acid, lauric acid, myristic acid, palmitic acid, stearic acid, etc., and mixtures thereof can be mentioned. Particularly preferred are saturated $C_{12}$–$C_{18}$ fatty acids, among which stearic acid is especially useful.

Where necessary, the percutaneously absorbable preparation of this invention may further contain the common additives which are generally used in the formulation of drug products, typically an excipient, a coloring agent, a solubilizer, and so on.

As to the solubilizer mentioned above, in particular, hydrophilic solvents such as polyhydric alcohols, e.g. propylene glycol, polyethylene glycol, glycerin, etc., and monohydric alcohols, e.g. ethyl alcohol, isopropyl alcohol, etc., including mixtures thereof can be employed.

Furthermore, long-chain or cyclic esters such as isopropyl myristate, diethyl sebacate, diisopropyl adipate, propylene carbonate, etc. can also be mentioned.

The percutaneously absorbable preparation of this invention can be provided in the form of an ordinary ointment. The ointment base that can be used includes vegetable or animal waxes (e.g. bleached beeswax, carnauba wax, beeswax, etc.), paraffins (e.g. paraffin, liquid paraffin, etc.), and petrolatums (e.g. white petrolatum etc.), among others. These bases can be used in the form of a mixture. Moreover, this preparation can be provided in the form of an ordinary cream, gel, plaster or lotion as well.

The proportion of said percutaneous absorption accelerator in the dosage form is 1–50 weight % and preferably 5–20 weight %.

The percutaneously absorbable preparation of this invention can be manufactured by, typically, dissolving a drug in propylene glycol or the like and mixing the solution with said monoglyceride and fatty acid, where necessary followed by addition of conventional additives.

While the drug that can be used in this invention is not particularly limited in kind but includes a broad variety of substances, there can typically be mentioned therapeutic agents for infectious diseases, such as antibiotics and antiviral agents, antiasthmatics, analgesics, antiinflammatory agents, antianginal agents, and neuroleptic agents, among other drugs. Particularly suitable, among them, are the compounds described in the following literature and known to have such pharmacologic activities as antitachykinin activity, particularly substance P-antagonizing activity, neurokinin A-antagonizing activity and neurokinin B-antagonizing activity, and be particularly useful for the treatment or prevention of pain.

The compound described in JP Kokai 4-210996:

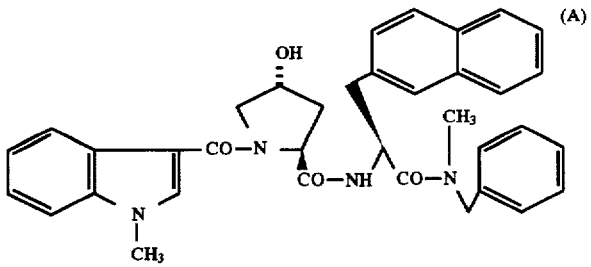

The compound described in JP Kokai 2-204499:

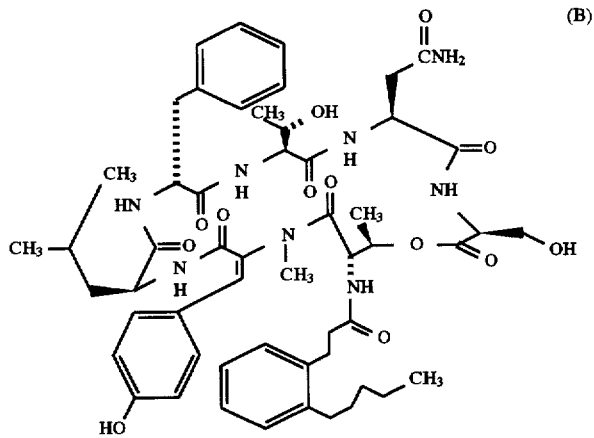

The compound described in WO 93/21215:

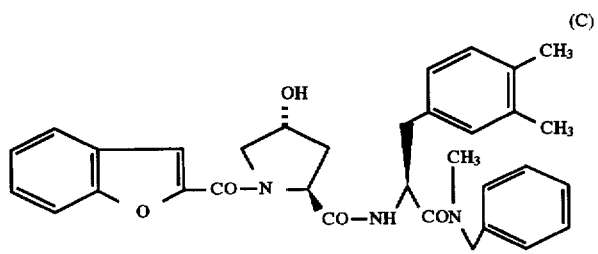

Another preferred example is the following compound which is described in JP Kokai 61-148181 as being of value as an immunosuppressant.

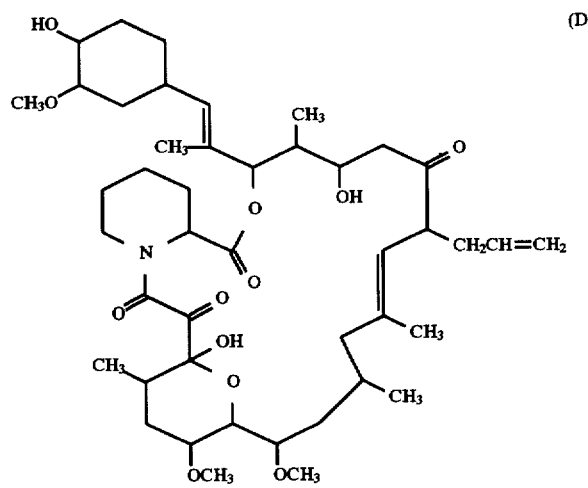

EXAMPLES

The following examples are further illustrative of this invention.

Example b 1

Compound (A) (1 part by weight) is added to propylene glycol (5 parts by weight) and the mixture is heated to 75 C. for dissolution. To this propylene glycol solution of compound (1) are added monolaurin (10 parts by weight), stearic acid (1 part by weight), bleached beeswax (3 parts by weight), liquid paraffin (40 parts by weight), and white petrolatum (40 parts by weight) and the mixture is heated at 75 C. for dissolution. The above mixture is placed in an agitator-homomixer (homomixer: 5000 rpm, paddle mixer 30 rpm, agitation time 10 min.) set to an internal temperature of 75±2 C. and agitated. Then, under agitation at a homomixer speed of 3000 rpm and a paddle mixer speed of 30 rpm, the internal temperature of the machine is lowered to 45±2 C. Thereafter, the agitation is continued by driving the paddle mixer alone at a speed of 18 rpm until the temperature level of 40±2 C. has been reached to complete preparation of an ointment.

Example 2

Ointments are manufactured according to the following recipes in otherwise the same manner as Example 1.

| (1) | Compound (A) | 1 part by weight |
|---|---|---|
| | Propylene glycol | 5 parts by weight |
| | Monolaurin | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (2) | Compound (A) | 1 part by weight |
| | Propylene glycol | 5 parts by weight |
| | Monoolein | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (3) | Compound (A) | 1 part by weight |
| | Propylene glycol | 5 parts by weight |
| | Monocaprin | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (4) | Compound (B) | 1 part by weight |
| | Propylene glycol | 5 parts by weight |
| | Monolaurin | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (5) | Compound (B) | 1 part by weight |
| | Propylene glycol | 5 parts by weight |
| | Monoolein | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (6) | Compound (B) | 1 part by weight |
| | Propylene glycol | 5 parts by weight |
| | Monocaprin | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (7) | Compound (C) | 1 part by weight |
| | Propylene glycol | 5 parts by weight |
| | Monolaurin | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |

-continued

| | | |
|---|---|---|
| (8) | Compound (C) | 1 part by weight |
| | Propylene glycol | 5 parts by weight |
| | Monoolein | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (9) | Compound (C) | 1 part by weight |
| | Propylene glycol | 5 parts by weight |
| | Monocaprin | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (10) | Compound (D) | 1 part by weight |
| | Propylene glycol | 5 parts by weight |
| | Monolaurin | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (11) | Compound (D) | 1 part by weight |
| | Propylene glycol | 5 parts by weight |
| | Monoolein | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |
| (12) | Compound (D) | 1 part by weight |
| | Propylene glycol | 5 parts by weight |
| | Monocaprin | 10 parts by weight |
| | Stearic acid | 2 parts by weight |
| | Bleached beeswax | 6 parts by weight |
| | Liquid paraffin | 35 parts by weight |
| | White petrolatum | 42 parts by weight |
| | | 101 parts by weight |

Reference Example 1

Ointments are prepared according to the following recipes in otherwise the same manner as Example 1.

| | | |
|---|---|---|
| (1) | Compound (A) | 1 part by weight |
| | Propylene glycol | 5 parts by weight |
| | Bleached beeswax | 10 parts by weight |
| | Liquid paraffin | 35 parts by weight |
| | White petrolatum | 49 parts by weight |
| | | 100 parts by weight |
| (2) | Compound (A) | 1 part by weight |
| | Propylene glycol | 5 parts by weight |
| | Monolaurin | 10 parts by weight |
| | Bleached beeswax | 3 parts by weight |
| | Liquid paraffin | 42 parts by weight |
| | White petrolatum | 39 parts by weight |
| | | 100 parts by weight |
| (3) | Compound (A) | 1 part by weight |
| | Propylene glycol | 5 parts by weight |
| | Monoolein | 10 parts by weight |
| | Bleached beeswax | 8 parts by weight |
| | Liquid paraffin | 37 parts by weight |
| | White petrolatum | 39 parts by weight |
| | | 100 parts by weight |

EFFECTS OF INVENTION

The cutaneous penetration of drugs could be enhanced with the percutaneously absorbable preparation of this invention.

The following percutaneous absorption test data are presented as evidence for the beneficial effect that accrues from the use of the preparation of this invention.

(I) Test dosage forms (a) The dosage form obtained in Reference Example 1-(1)

(b) The dosage form obtained in Reference Example 1-(2)

(c) The dosage form obtained in Reference Example 1-(3)

(d) The dosage form obtained in Example 1

(e) The dosage form obtained in Example 2-(1)

(II) Method

The abdomen of rats (SD strain, 7–8 weeks old, average body weight ca. 250 g) was clipped of hairs and after an interval of 24 hours, 100 mg of the test dosage form was applied to a 10 cm square area of the abdominal skin. Blood was drawn serially from the subclavian vein and centrifuged to separate the plasma and the plasma drug concentration was determined by high performance liquid chromatography.

(III) Results

The areas under the plasma concentration-time curves $(AUC_{0-24})$ are shown in the following table.

| Test dosage form | $AUC_{0-24}$ (ng hr/ml) |
|---|---|
| (a) | 0 |
| (b) | 215 |
| (c) | 118 |
| (d) | 1341 |
| (e) | 1656 |

It is apparent from the above percutaneous absorption test data that the dosage forms (d) and (e) of this invention have been remarkably improved in the degree of cutaneous penetration of the active substance as compared with the monoglyceride-free dosage form (a). It is also apparent from comparison with the dosage forms (b) and (c) that causing a fatty acid to be present in conjunction with a monoglyceride leads to enhanced cutaneous penetration. Therefore, the percutaneously absorbable preparation of this invention is remarkably useful.

What is claimed is:

1. A percutaneously absorbable pharmaceutical composition, comprising:

1) a drug selected from the group consisting of those with the formulae:

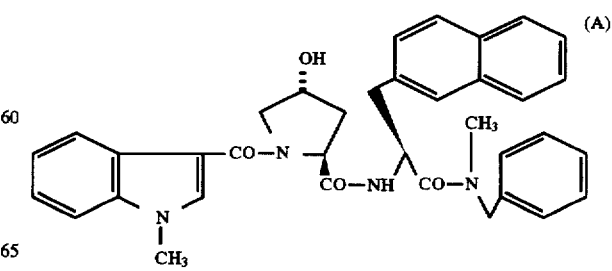

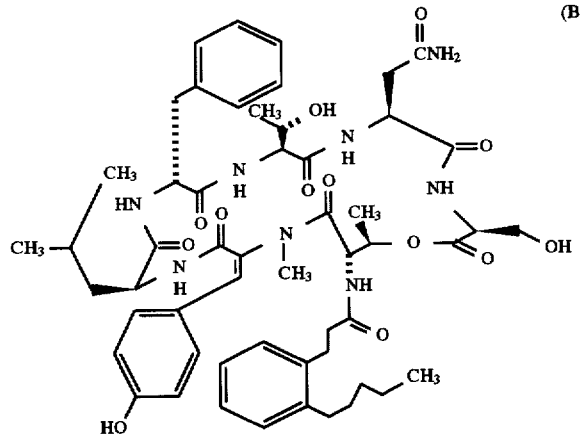

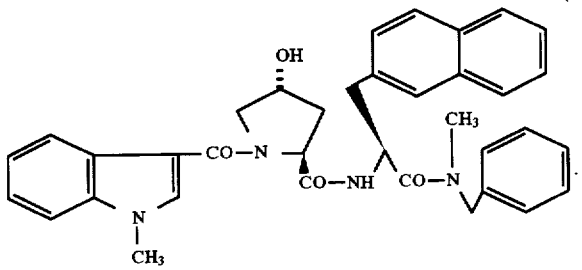

3. The percutaneously absorbable pharmaceutical composition of claim 1, wherein said drug has the formula:

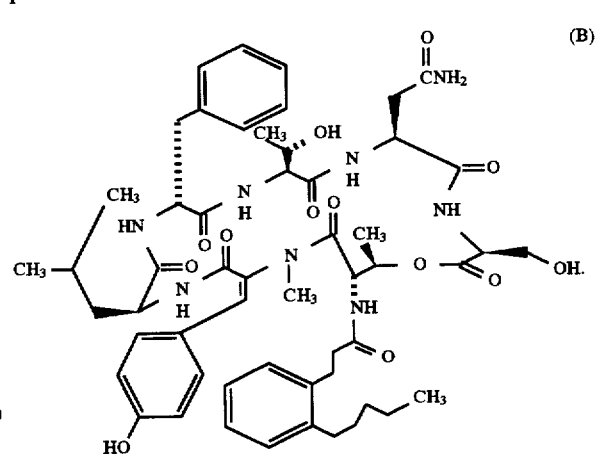

4. The percutaneously absorbable pharmaceutical composition of claim 1, wherein said drug has the formula:

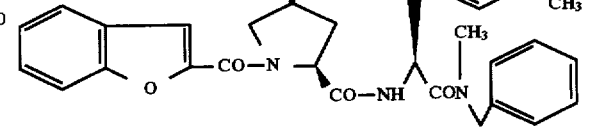

5. The percutaneously absorbable pharmaceutical composition of claim 1, wherein said drug has the formula:

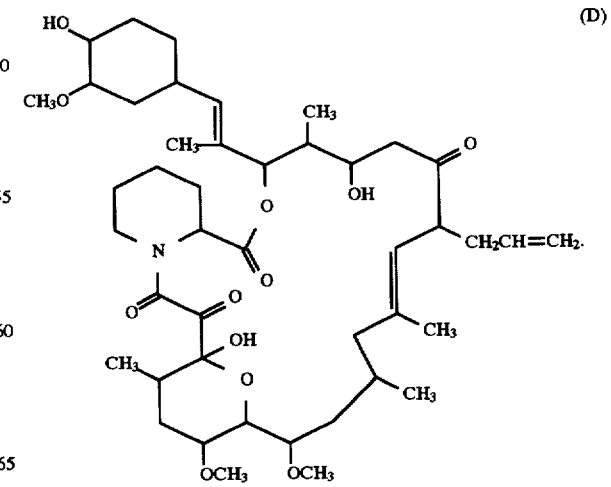

2) a percutaneously absorption accelerator, comprising:
a) a monoglyceride selected from the group consisting of monocaprin, monolaurin, monomyristin, monopalmitin, monostearin and monoolein; and
b) a fatty acid selected from the group consisting of capric acid, lauric acid, myristic acid, palmitic acid and stearic acid.

2. The percutaneously absorbable pharmaceutical composition of claim 1, wherein said drug has the formula:

6. The percutaneously absorbable pharmaceutical composition of claim 1, wherein said monoglyceride is selected from the group consisting of monocaprin, monolaurin and monoolein.

7. The percutaneously absorbable pharmaceutical composition of claim 1, wherein said fatty acid is stearic acid.

8. The percutaneously absorbable pharmaceutical composition of claim 1, which further comprises an excipient, coloring agent or solubilizer.

9. The percentaneously absorbable pharmaceutical composition of claim 8, wherein said solubilizer is selected from the group consisting of propylene glycol, polyethylene glycol, glycerin, ethyl alcohol, isopropyl alcohol, isopropyl myristate, diethyl sebacate, diisopropyl adipate and propylene carbonate.

10. The percutaneously absorbable pharmaceutical composition of claim 1, which is in a form of an ointment, cream, gel, plaster or lotion.

* * * * *